(12) United States Patent
Ignon

(10) Patent No.: US 6,629,983 B1
(45) Date of Patent: Oct. 7, 2003

(54) APPARATUS AND METHOD FOR SKIN/SURFACE ABRASION

(75) Inventor: Roger G. Ignon, Redondo Beach, CA (US)

(73) Assignee: Edge Systems Corporation, Signal Hill, CA (US)

( * ) Notice: Subject to any disclaimer, the term of this patent is extended or adjusted under 35 U.S.C. 154(b) by 206 days.

(21) Appl. No.: 09/699,220

(22) Filed: Oct. 27, 2000

(51) Int. Cl.[7] .............................................. A61B 17/50
(52) U.S. Cl. ...................................................... 606/131
(58) Field of Search ................................ 606/131, 132, 606/133

(56) References Cited

U.S. PATENT DOCUMENTS

| | | | | |
|---|---|---|---|---|
| 2,701,559 A | 2/1955 | Cooper | ............ | 128/2 |
| 2,712,823 A | 7/1955 | Kurtin | ............ | 128/303 |
| 2,867,214 A | 1/1959 | Wilson | ............ | 128/355 |
| 2,881,763 A | 4/1959 | Robbins | ............ | 128/355 |
| 2,921,585 A | 1/1960 | Schumann | ............ | 128/355 |
| 3,964,212 A | 6/1976 | Karden | ............ | 51/170 |
| 4,378,804 A | 4/1983 | Cortese, Jr. | ............ | 128/355 |
| 4,572,187 A | * 2/1986 | Schetrumpf | ............ | 606/131 |
| 4,957,747 A | 9/1990 | Stiefel | ............ | 424/691 |
| 5,012,797 A | 5/1991 | Liang et al. | ............ | 128/24 |
| 5,037,431 A | 8/1991 | Summers et al. | ............ | 606/131 |
| 5,037,432 A | 8/1991 | Molinari | | |
| 5,100,412 A | 3/1992 | Rosso | | |
| 5,207,234 A | 5/1993 | Rosso | | |
| 5,354,307 A | * 10/1994 | Porowski et al. | ............ | 606/171 |
| 5,800,446 A | 9/1998 | Banuchi | ............ | 606/131 |
| 5,810,842 A | 9/1998 | Di Fiore et al. | | |
| 5,954,730 A | 9/1999 | Bernabei | | |
| 5,971,999 A | 10/1999 | Naldoni | | |
| 6,019,749 A | 2/2000 | Fields et al. | | |
| 6,039,745 A | 3/2000 | Di Fiore et al. | | |
| 6,042,552 A | 3/2000 | Cornier | ............ | 600/562 |
| 6,080,165 A | 6/2000 | DeJacma | | |
| 6,162,232 A | * 12/2000 | Shadduck | ............ | 606/131 |
| 6,299,620 B1 | * 10/2001 | Shadduck et al. | ............ | 606/131 |
| 6,391,034 B1 | * 5/2002 | Adamson et al. | ............ | 606/131 |
| 6,423,078 B1 | * 7/2002 | Bays et al. | ............ | 606/131 |
| 6,432,113 B1 | * 8/2002 | Parkin et al. | ............ | 606/131 |

* cited by examiner

Primary Examiner—Michael Peffley
(74) Attorney, Agent, or Firm—Richard L. Myers; Myers Dawes Andras & Sherman

(57) ABSTRACT

A dermabrasion handpiece adapted for use to abrade the skin of a patient includes a housing extending along an axis between a proximal end and a distal end. Portions of the housing define a hole at the distal end with an abrasion element disposed in the housing in proximity to the hole. The housing is adapted for connection to a vacuum source to pull a portion of the skin through the hole and to move the skin portion into contact with the abrasion element. Movement of the abrader relative to the skin abrades tissue from the skin portion extending through the hole. The abrader can be provided in the form of a roller or blade moveable relative to the housing to abrade the skin. The abrasion element can be selected from a series of elements each having different abrasion characteristics and can be mounted in either the cap or the base of the housing.

22 Claims, 4 Drawing Sheets

US 6,629,983 B1

APPARATUS AND METHOD FOR SKIN/SURFACE ABRASION

BACKGROUND OF THE INVENTION

1. Field of the Invention

This invention relates generally to skin or surface abrasion apparatus and methods, and more specifically to semi-automatic handpieces used in dermabrasion.

2. Discussion of the Prior Art

It is often desirable to abrade the outer layer or epidermis of the skin in order to smooth or blend scars, or blemishes caused by acne for example. The techniques employed have been separated generally into two fields referred to as dermabrasion and microdermabrasion. With microdermabrasion, a sand or grit is carried by an air flow which is directed against the skin. The momentum of the grit tends to wear away two to three cell layers of the skin with each pass of a handpiece.

Dermabrasion refers generally to the mechanical movement of an abrasive element against the skin. A handpiece is employed which may include a pneumatic or electric motor which drives the abrasive element typically in the form of a burr, wheel, or disk. This process tends to be relatively painful and messy.

Dermabrasion has also been accomplished using a semi-automatic handpiece having a grit fixed to its outer surface. The handpiece is then moved over the skin causing the grit to abrade the cell layers. Suction has been applied to the semi-automatic handpiece through a hole which extends to the outer surface carrying the grit. As the skin is drawn into the hole, it is also pulled against the grit surrounding the hole on the outer surface of the handpiece. This is also a fairly messy procedure since the abrasion takes place outside of the handpiece. In this device, no attempt has been made to use the suction to remove the debris.

SUMMARY OF THE INVENTION

In accordance with the present invention, a semi-automatic handpiece is disclosed which uses suction to clear the debris from the operative site. Suction is applied to the handpiece to draw skin through a hole and into the handpiece. Within the handpiece, this skin extending through the hole is drawn onto an abrasive surface. As the handpiece is moved over the skin, progressive areas of the skin are drawn into the handpiece and abraded. This suction also creates a seal with the outer edges of the hole so debris abraded from the skin interiorly of the handpiece can be drawn away by the suction.

The abrasive element within the handpiece can be made disposable so that a new abrasion element is available for each reuse of the handpiece. A set of abrasive elements can be provided with different abrasion characteristics to provide for coarse and fine adjustments in the process. The handpiece can be formed with a housing having a body and a cap removable from the body to access the abrasive element.

In one aspect of the invention a dermabrasion handpiece is adapted for use in abrading the skin of a patient. The handpiece includes a housing extending along an axis between a proximal end and a distal end. Portions of the housing define a hole at the distal end of the handpiece. An abrasion element is disposed in the housing in proximity to the hole. The housing is adapted for connection to a vacuum source so that, in operation, a portion of the skin is drawn through the hole and moved into contact with the abrasion element. Movement of the handpiece relative to the skin abrades tissue from the skin portion extend through the hole.

In another aspect of the invention, a method for abrading the skin of the patient includes the step of providing a handpiece with a hole and moving a portion of the skin through the hole and into the handpiece. Ultimately, the skin portion moved through the hole of the handpiece is abraded within the handpiece.

In a further aspect of the invention a method for operating a skin abrader includes the steps of providing a housing with a base and a cap separable to provide access to an abrasion element within the housing. A series of abrasion elements is provided, each having different abrasion characteristics. From this series, a particular one of the elements can be chosen for the specific abrasion characteristics described. The cap is removed from the base and the chosen element is mounted within the cap or the base. The cap is then replaced on the base with the abrasion element disposed in the housing.

DESCRIPTION OF PREFERRED EMBODIMENTS AND BEST MODE OF THE INVENTION

Figure 1:
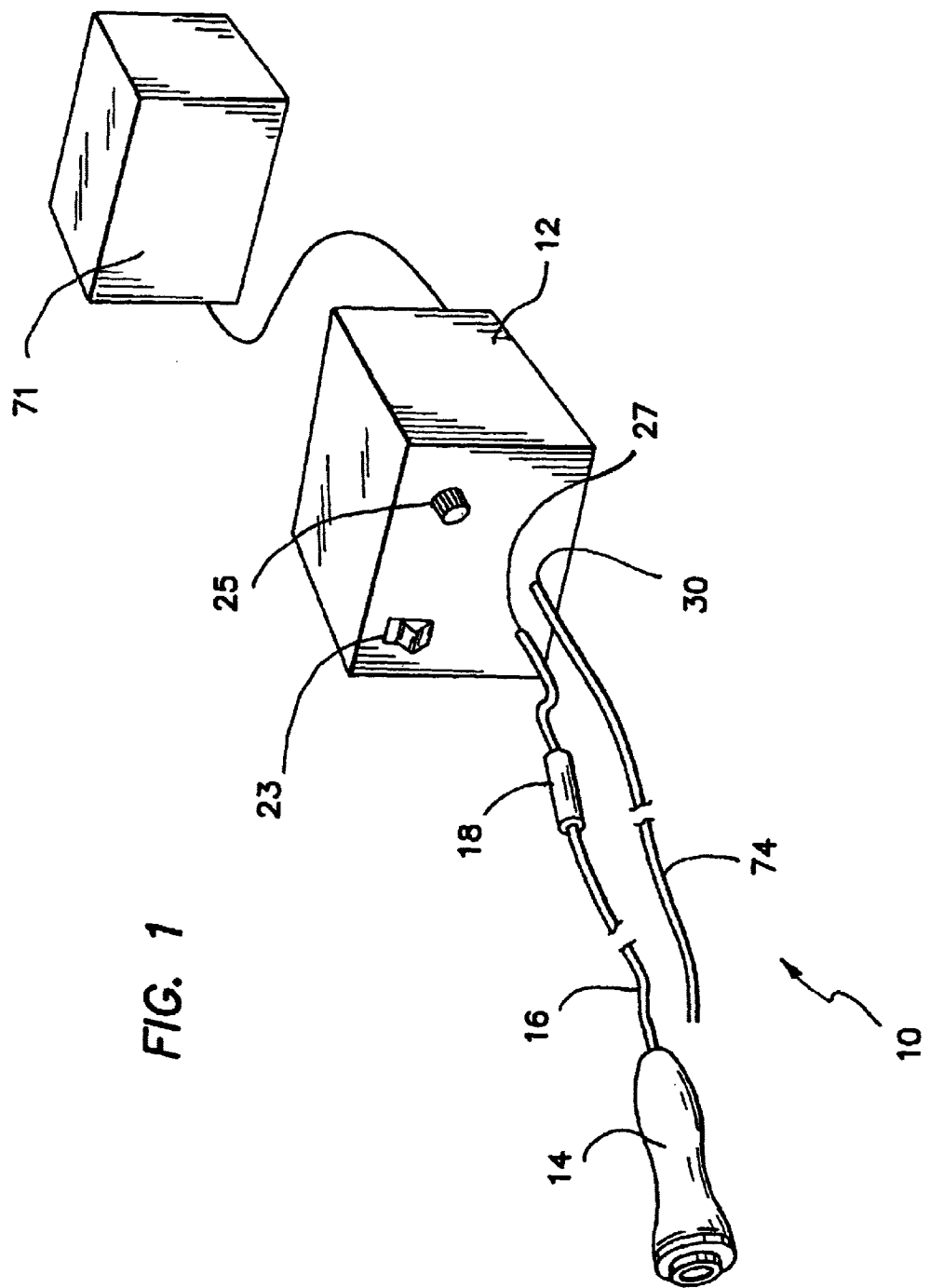
FIG. 1 is a schematic view of a dermabrader including a console and a handpiece associated with the present invention.

A dermabrader is illustrated in FIG. 1 and designated by the reference numeral 10. The dermabrader 10 includes a console 12, and a handpiece 14 connectable to the console 12 through a vacuum tube 16 having an inline filter 18. The console 12 in this case is powered by a 12 volt transformer 21 and includes a power switch 23 and a vacuum adjustment 25. Releasable connectors are provided at a vacuum port 27 and a pressure port 30 discussed in greater detail below.

Figures 2, 3:
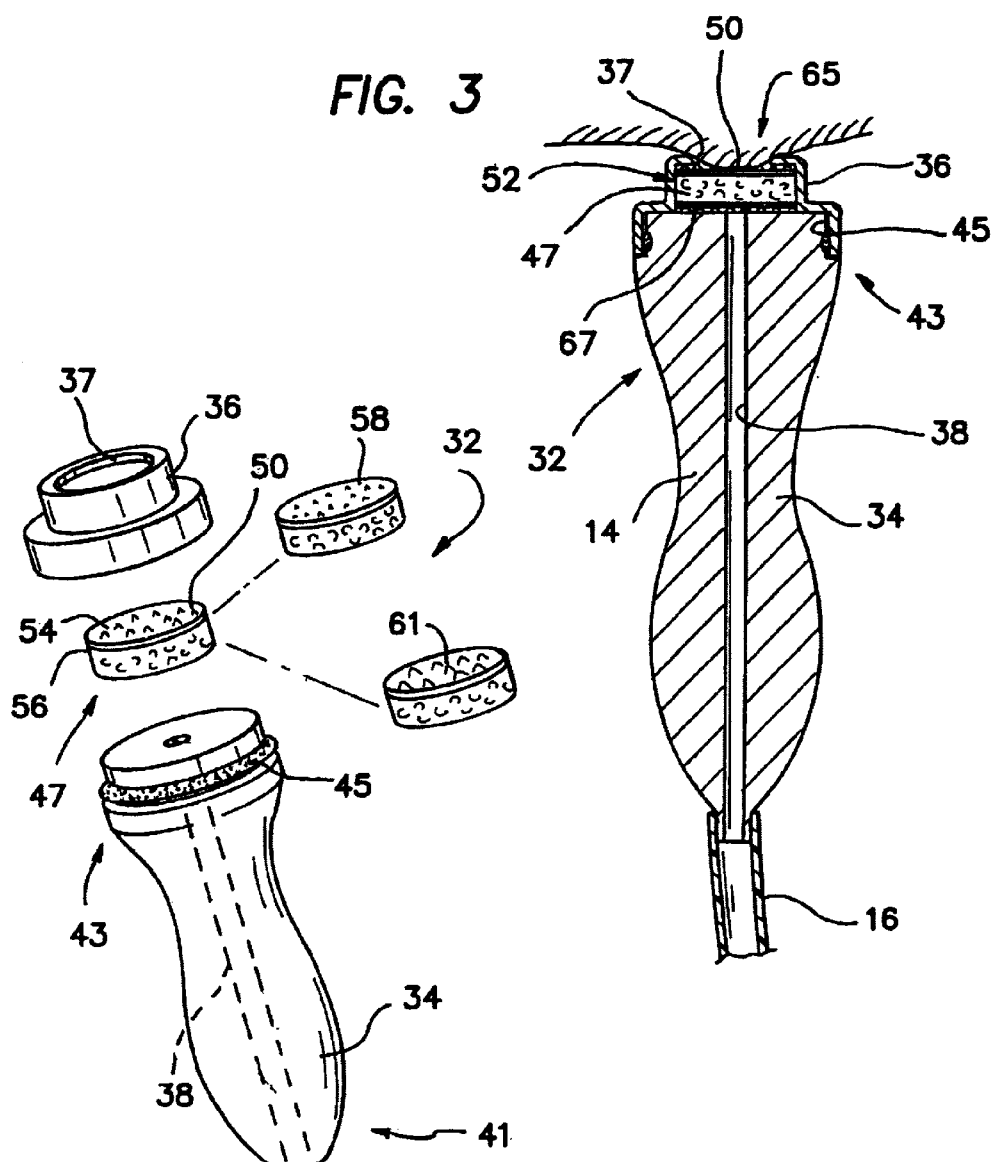
FIG. 2 is a exploded perspective view of one embodiment of the handpiece of the present invention.
FIG. 3 is an axial cross-section view of the handpiece operatively disposed relative to the skin of a patient.

The handpiece 14, which is shown in the exploded view of FIG. 2, includes a housing 32 which in this embodiment is formed by base 34 and a cap 36 having an opening 37. The base 34 has a central channel 38 extending between a proximal end 41 and a distal end 43. At the proximal end 41, the channel 38 is coupled to the vacuum tube 16; at the distal end 43, the cap 36 is attached to the base 34 in a snap-fit relationship. This configuration is facilitated by provision of an O-ring 45 at the distal end 43.

Of particular interest to the present invention is an abrasive disc or element 47 which is disposed between the cap 36 and the base 34. In this embodiment, the element 47 includes a laminate having an abrasive layer 50 and a resilient layer 52. The abrasive layer 50 includes an abrasive grit 54 adhered to a backing 56 which may be porous. The resilient layer 52 in this embodiment is formed a resilient sponge material. In practice, the abrasive element 47 may be provided as a series of elements having a similar construction but differing in the size of the grit 54 and hence the abrasive characteristics of each element 47. In FIG. 2, these alternative elements which provide different abrasion characteristics are designated by the reference numerals 58 and 61.

An assembled view of the handpiece 14 is illustrated in FIG. 3. In this cross-sectional view, the handpiece 14 illustrated to be operatively disposed relative to skin 63 of a patient. With this disposition of the handpiece 14, vacuum can be applied by the console 12 (FIG. 1) to the tube 16 and through the channel 38 to the distal end 43 of the base 34. At this point, the vacuum provides suction around and/or through the abrasive disk or element 47 to the opening 37 in the cap 36; When this opening 37 in the handpiece 14 is brought into proximity with the skin 63, a portion of the skin, designated by the reference numeral 65, is drawn through the opening 37 and into abrasive contact with the disk or element 47. It is of particular interest that abrasion occurs only with respect to the skin portion 65 which is drawn through the opening 37. This insures that any debris resulting from the abrasion is exposed to the vacuum and drawn off into the channel 38 and vacuum tube 16.

In this embodiment abrasion occurs not simply due to contact between the skin portion 65 and the abrasive element 47, but due to the relevant movement of the skin portion 65 and the element 47 as the handpiece 14 is moved over the skin 63. Thus, progressive portions of the skin 63 are drawn into abrasive contact with the element 47 as the handpiece 14 is moved relative to the surface or skin 63.

In a particular embodiment, the abrasive layer 50 may be fixed and rigid relative to the cap 36 and the base 34. This orientation tends to produce abrasion that is dependent only upon the force applied to the handpiece 14 by the user. In order to create a more uniform pressure, and therefore more uniform abrasion, a preferred embodiment includes the layer 52 which provides a flexible backing and hence more resilient characteristics for the abrasion layer 50. In FIG. 3, the abrasive disk or element 47 differs from that previously discussed in that it includes a second abrasive layer 67 on the opposite side of the resilient layer 52. With this configuration, the pad can be reversed to provide a new abrasive surface with the same size of grit, or alternatively to provide an abrasive surface which has a different size of grit.

Figure 4:
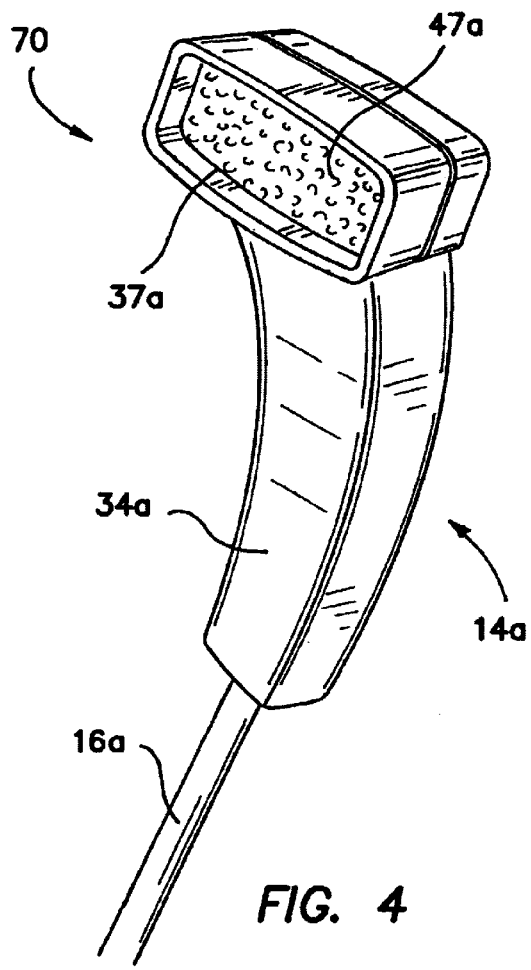
FIG. 4 is a perspective view of a further embodiment of the handpiece of the present invention.

An additional embodiment of the invention is illustrated in FIG. 4 where elements of similar structure are designated by the same reference numeral followed by the lower case letter "a". Thus, the handpiece 14a is coupled to the vacuum tube 16a. However, in this case, the handpiece 14a has a base 34a and a head 70 which are integrally molded, perhaps from plastic. The head 70 includes an opening 37a which in this embodiment has a rectangular configuration. An abrasive surface is provided by the abrasive element 47a which also has a rectangular configuration. The element 47a in this case can be glued on or snapped into the head 70.

Figures 5, 6:
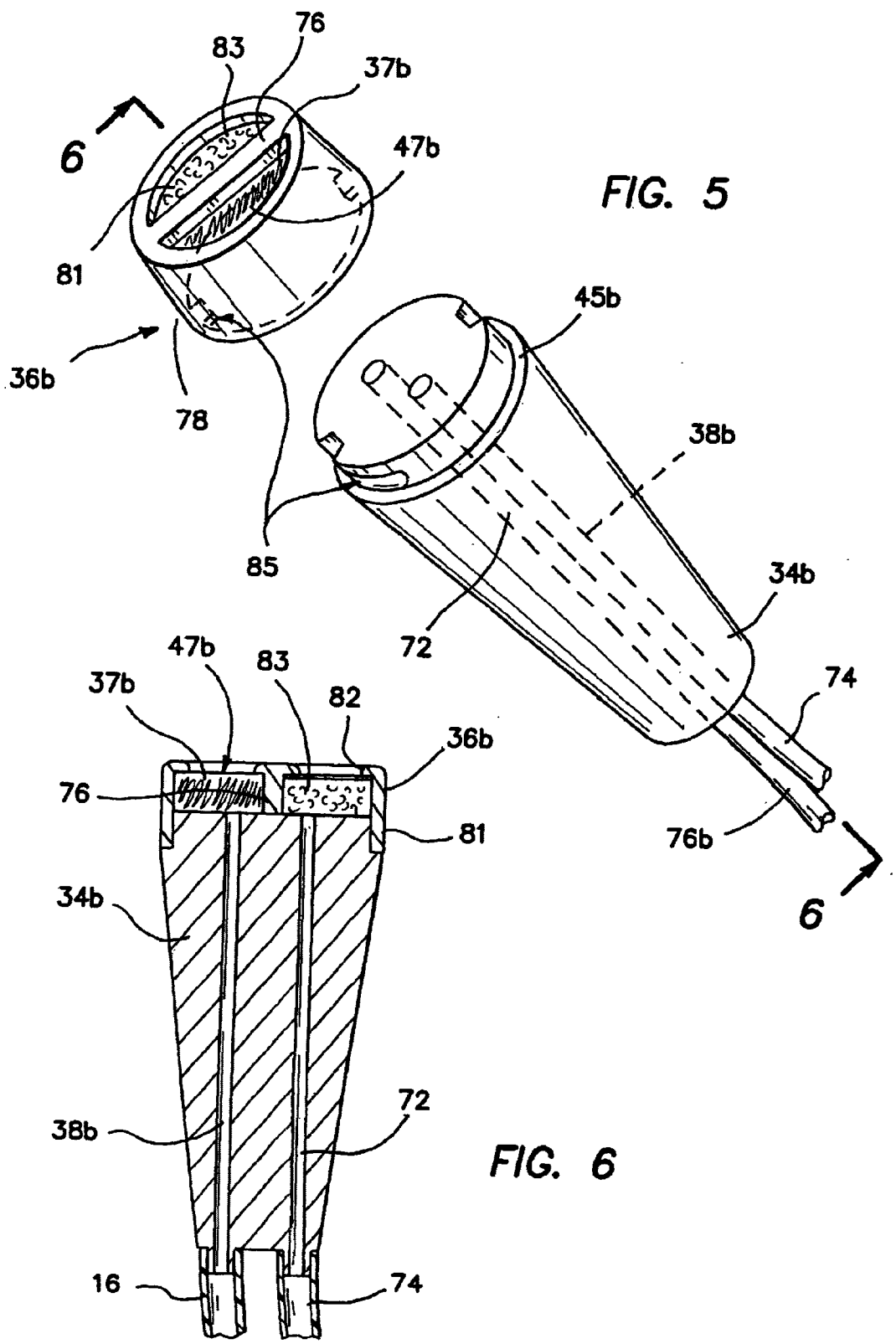
FIG. 5 is an exploded view of a further embodiment of the handpiece of the present invention.
FIG. 6 is an axial cross-section view taken-along lines 6—6 of FIG. 5.

A further embodiment of the invention is illustrated in FIG. 5 wherein elements of similar structure are designated by the same reference numeral followed by the lower case letter "b". Thus, this embodiment includes a base 34b defining a channel 38b which is in fluid communication with the vacuum tube 16b. In this case, the base 34b also defines a second channel 72 which is spaced from the channel 38b. The channel 72 is adapted for connection to the pressure tube 74 which is illustrated in FIG. 5 and also in the system view of FIG. 1.

The cap 36b includes a septum 76 which divides the cap 36b into two chambers, an abrasion chamber 78 communicating with the vacuum channel 38b, and a chemical chamber 81 having an opening 82 and communicating with the pressure channel 72. Disposed within the abrasion chamber 78 is the abrasion element 47b previously discussed. In the chemical chamber 81, a sponge or pad 83 can be impregnated with a chemical such as vitamin C or vitamin A. In this embodiment, the cap 36b can be snap-fit to the base 34b in the manner previously discussed or attached with a bayonet fitting 85. Both the pad 83 and abrasive element 37b could be combined in a single disposable element.

A cross-section view of the embodiment of FIG. 5 is illustrated in FIG. 6. In operation, the vacuum tube 16b, channel 38b, opening 37b, and abrasive element 47b function in the manner previously disclosed. However in this embodiment, pressurized air is introduced into the tube 72 and the chemical chamber 81 to force any chemical impregnated in the sponge 83 outwardly through the opening 82. This ensures that the chemical, such as vitamin A or vitamin C, is introduced onto the abraded area of the skin.

Figure 7:
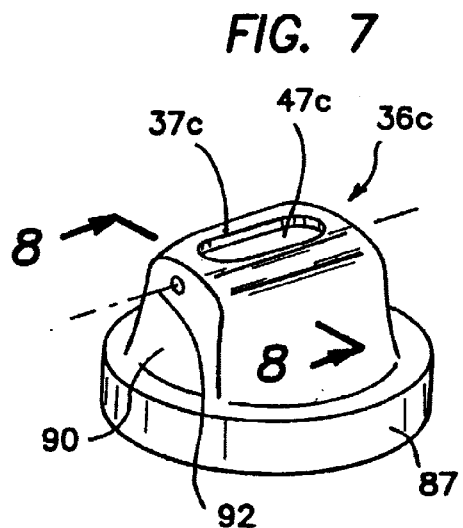
FIG. 7 is a perspective view of another embodiment of the handpiece of the present invention.
Figure 8:
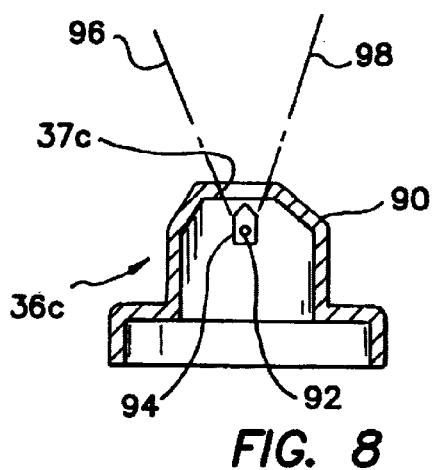
FIG. 8 is a cross-sectional view taken along lines 8—8 of FIG. 7.
Figure 9:
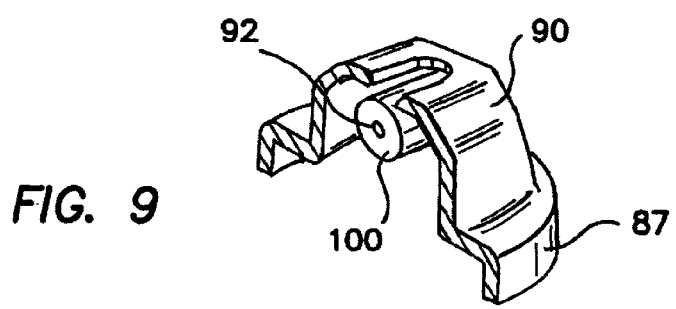
FIG. 9 is a cross-sectional view similar to FIG. 8 and illustrating a further embodiment the handpiece of the present invention

Further embodiments of the invention are illustrated in FIGS. 7–9 wherein abrasive elements are discussed which move relative to the handpiece. In the embodiment of FIGS. 7 & 8, elements of structure similar to those previously disclosed are designated with the same reference numeral followed by the lower case letter "c". Similarly, in the embodiment of FIG. 9, these structural elements are followed by the lower case letter "d".

Referring to the embodiment of FIG. 7, the cap 36c includes a skirt 87 and a projection 90 which extends to the opening 37c. The skirt 87 can provide a snap-fit, screw, or bayonet attachment to the base 34 (FIG. 2). The opening 37c in the projection 90 is longitudinal in configuration to provide the greatest exposure to a longitudinal abrasion element which is supported on a shaft 92 which is fixed at its ends to the projection 90. The abrasion element 47c in this case is provided in the form of a blade 94 best illustrated in the cross-section view of FIG. 8. As noted, the blade 94 is pivotal with or on the shaft 92 relative to the cap 36c. The blade 94 may oscillate under the power of the vacuum or pressurized air. Alternatively, the blade 94 may be moveable by mere contact with the skin 63 between terminal positions shown by the lines 96 and 98 in FIG. 8. In this embodiment, the blade 94 functions as a scraper as it is drawn along the skin 63 (FIG. 3).

In the embodiment of FIG. 9, an abrasive wheel 100 is mounted on the shaft 92. The wheel 100 may be fixed to the projection 90 so that it does not move relative to the skin 63 (FIG. 3) but rather is stationary and therefore abrasive to the skin 63. The wheel 100 can be indexed however to expose different portions of the wheel 100 so that a new abrasive surface faces the opening 37c as the wheel is indexed.

Alternatively, the wheel 100 can be rotated under the power of the vacuum or pressurized air from the console 12 (FIG. 1) which might be applied, for example, to an impeller (not shown) associated with the roller 100.

What is claimed is:

1. A surface abrasion handpiece adapted for use to abrade skin of a patient, comprising:

a housing extending along an axis between a proximal end and a distal end;

portions of the housing defining a hole at the distal end of the housing;

an abrasion element disposed in a plane retained by the housing in proximity to the hole;

the housing being separable between the proximal end and the distal end to provide access into the housing to facilitate insertion of the abrasion element into the housing and removal of the abrasion element from the housing;

the housing being adapted for connection to a vacuum source to pull a portion of the skin through the hole and to move the skin portion into contact with the abrasion element; whereby movement of the handpiece relative to the skin abrades tissue from the skin portion extending through the hole.

2. The handpiece recited in claim 1 wherein the abrasion element includes an abrasive surface disposed relative to the hole.

3. The handpiece recited in claim 2 wherein the abrasion element includes:

a disc having a generally planar outer surface; and the abrasive surface is formed on the outer surface of the disc.

4. The handpiece recited in claim 3, wherein:

the portions defining the hole are disposed generally in a particular plane; and the outer surface of the disc is generally parallel to the particular plane.

5. The handpiece recited in claim 2, wherein:

the abrasion element includes a roller having a generally cylindrical outer surface; and the abrasive surface forms the outer surface of the roller.

6. The handpiece recited in claim 1, wherein the abrader includes a blade disposed in proximity to the hole, the blade being movable relative to the housing.

7. The handpiece recited in claim 6, wherein:

the blade is moveable between a first position and a second position;

the blade in the first position being adapted for scraping the skin with movement of the housing is a first direction; and the blade in a second position being adapted for scraping the skin with movement of the housing in a second direction opposed to the first direction.

8. The handpiece recited in claim 7, wherein the blade is pivotal relative of the housing between the first position and the second position.

9. A dermabrader for use on the skin of a patient, comprising:

a handpiece having:
a housing,
a cap releasably mounted on the housing,
an opening defined generally in a particular plane by at least one of the housing and the cap; and
an abrasion element removable from the housing and the cap, the element being retained by the cap in proximity to the opening;

a vacuum adapted to move a portion of the skin through the opening and into the handpiece, and to further move the portion of the skin into contact with the abrasion element.

10. The dermabrader of claim 9, wherein:

the abrasion element comprises an abrasion surface in proximity to the opening;

the opening is defined by a continuous edge disposed in the particular plane and adapted to form a seal with the skin of the patient; and the vacuum moves the skin relative to the abrasion surface to abrade the portion of the skin.

11. The dermabrader recited in claim 10, wherein:

the seal is disposed in a claim; and the abrasive surface is generally parallel to the plane of the seal.

12. The dermabrader of claim 9, wherein the abrasion element includes a first abrasion surface and an opposing second abrasion surface, and has properties for being selectively movable to expose only one of the abrasion surfaces through the opening.

13. The dermabrader of claim 9, further comprising means for moving the abrasion element relative to the handpiece.

14. A skin abrasion system for abrading the skin of a patient, comprising:

a handpiece having:
a housing including a base and a cap;
portions of one of the base and the cap defining an opening, generally in a particular plane;
at least one abrasion element removably disposed in the handpiece proximate to the opening; and
a source of vacuum connected to the handpiece in fluid communication with the opening to draw the skin of the patient through the opening and into contact with the abrasion element.

15. The system of claim 14, wherein:

the opening is defined by smooth edges that are adapted to form a seal with the skin of the patient to facilitate movement of successive portions of the skin through the opening by means of suction as the handpiece is moved along the skin of the patient.

16. The system of claim 14, wherein:

the abrasion element has a pivotal relationship with a least one of the cap and the base;

the abrasion element has a first terminal position and a second terminal position; and the abrasion element is adapted for oscillating movement between the first and second terminal positions.

17. The system of claim 16, further comprising:

a source of pressurized air; and means coupled to the source of pressurized air for oscillating the abrasion element in abrading contact with the portion of the skin.

18. The system of claim 14, wherein:

the cap is removably mounted on the base;

the at least one abrasion element is one of a plurality of abrasion elements, each abrasion element having different abrasion characteristics; and the cap holds a selected one of the abrasion elements on the handpiece.

19. The system of claim 14, further comprising:

the source of vacuum connected to the handpiece by a tube; and a filter connected to the tube.

20. A skin abrasion system for abrading the skin of a patient, comprising:

a handpiece having:
a housing including a base and a cap,
first portions of at least one of the base and the cap defining an opening, and
at least one abrasion element in the handpiece proximate to the opening; and a source of vacuum connected to the handpiece in fluid communication with the opening;

second portions of at least one of the base and the cap defining a second opening in communication with a chamber; and a pad impregnated with a chemical and disposed in the chamber, the pad being adapted to transfer the chemical to the skin of the patient.

21. The system of claim 20, further comprising:

a pressurized fluid coupled to the chamber and forcing the chemical from the pad in order to facilitate the transfer of the chemical onto the skin of the patient.

22. A dermabrader for use on the skin of a patient, comprising:

a handpiece having:

a housing, a cap releasably mounted on the housing, portions of at least one of the housing and the cap defining an opening, an abrasion element disposed in a plane enclosed in the handpiece by the cap; and means for progressively moving the skin of the patient through the opening and into contact with the abrasion element in the handpiece.

* * * * *